(12) United States Patent
Conley, Jr. et al.

(10) Patent No.: US 7,528,695 B2
(45) Date of Patent: May 5, 2009

(54) METHOD TO MANIPULATE SELECTIVITY OF A METAL OXIDE SENSOR

(75) Inventors: John F. Conley, Jr., Camas, WA (US); Yoshi Ono, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 626 days.

(21) Appl. No.: 11/361,519

(22) Filed: Feb. 23, 2006

(65) Prior Publication Data
US 2007/0193974 A1    Aug. 23, 2007

(51) Int. Cl.
*H01C 7/00* (2006.01)
(52) U.S. Cl. .................. 338/34; 257/E51.016; 438/57
(58) Field of Classification Search ............ 338/34; 257/E51.016, E51.029; 438/57, 104, 48, 438/99
See application file for complete search history.

(56) References Cited

OTHER PUBLICATIONS

Kolmakov et al., *Chemical sensing and catalysis by one-dimensional metal-oxide nanostructures*, Annu. Rev. Mater. Res. 34, 151 (2004).
Wang et al., *Hydrogen-selective sensing at room temperature with ZnO nanorods*, Appl. Phys. Lett. 86, 243503 (2005).
Woldena et al., *Infrared detection of hydrogen-generated free carriers in polycrystalline ZnO thin films*, Appl. Phys. Lett. 97, 043522 (2005).
U.S. Appl. No. 10/976,594, filed Oct. 29, 2004, Conley, Jr. et al.
U.S. Appl. No. 10/977,430, filed Oct. 29, 2004, Conley, Jr. et al.
U.S. Appl. No. 11/115,814, filed Apr. 26, 2005, Conley, Jr. et al.
U.S. Appl. No. 11/152,289, filed Jun. 13, 2005, Conley, Jr. et al.

Primary Examiner—Kyung Lee
(74) Attorney, Agent, or Firm—Law Office of Gerald Maliszewski; Gerald Maliszewski

(57) ABSTRACT

A method of selectively enhancing the sensitivity of a metal oxide sensor includes fabricating a ZnO sensor having a ZnO sensor element therein; and exposing the ZnO sensor element to a plasma stream.

7 Claims, 4 Drawing Sheets

METHOD TO MANIPULATE SELECTIVITY OF A METAL OXIDE SENSOR

FIELD OF THE INVENTION

This invention relates to metal oxide sensors, and specifically to a method of selectively enhancing sensor sensitivity by exposure to a hydrogen plasma.

BACKGROUND OF THE INVENTION

Metal oxides, such as ZnO, $In_2O_3$, $SnO_2$, ITO, etc., are well known to be sensitive to various ambients and have been employed as electronic gas sensors. The way these sensors work is via charge exchange between a nanowire and adsorbents at the nanowire surface. Due to their inherently high surface to volume ratio, sensors employing nanostructured metal oxides, e.g., nanowires, nanorods, nanobridges, etc., promise ultra high sensitivity. Although metal oxides have been demonstrated to be sensitive to many gases, e.g., $O_2$, $H_2O$, ethanol, methanol, CO, $NO_2$, $NH_3$, etc., one of the great challenges of using these materials is selectivity, or how well a sensor can differentiate the gas of interest from background gases. Kolmakov et al., *Chemical sensing and catalysis by one-dimensional metal-oxide nanostructures*, Annu. Rev. Mater. Res. 34, 151 (2004).

Currently, several methods have been shown to be at least partially effective in improving sensitivity, such as bias control in a back gated device structure or the use of platinum or palladium nanoparticles to improve sensitivity to $H_2$, as described by Wang et al., *Hydrogen-selective sensing at room temperature with ZnO nanorods*, Appl. Phys. Lett. 86, 243503 (2005), which discusses careful control of operating temperature, the use of different metal oxide materials in an array, etc. None of these methods have proven to be ideal.

Our prior disclosures, entitled Selective growth of ZnO nanowires using a patterned ALD ZnO seed layer, and U.S. patent application Ser. No. 10/977,430, filed Oct. 29, 2004, and ALD ZnO seed layer for deposition of ZnO nanostructures on a Silicon substrate, U.S. patent application Ser. No. 10/976,594, also filed Oct. 29, 2004, describe processes for fabrication of metal oxide sensors, and are directed towards an integration method for forming nanobridge based ZnO sensors that involves selectively growing ZnO nanowires from one electrode to another, and are incorporated herein by reference.

SUMMARY OF THE INVENTION

A method of selectively enhancing the sensitivity of a metal oxide sensor includes fabricating a ZnO sensor having a ZnO sensor element therein; and exposing the ZnO sensor element to a plasma stream.

It is an object of the invention selectively to enhance the sensitivity of a nanowire sensor by application of a hydrogen plasma to the sensor structure.

This summary and objectives of the invention are provided to enable quick comprehension of the nature of the invention. A more thorough understanding of the invention may be obtained by reference to the following detailed description of the preferred embodiment of the invention in connection with the drawings.

DETAILED DESCRIPTION OF THE PREFERRED EMBODIMENTS

A method for selectively manipulating the sensitivity of metal oxide based sensors is disclosed, which involves treating the surface of the metal oxide with a plasma, and, in the preferred embodiment, treating the surface of a metal oxide sensor with a hydrogen plasma. The process may easily be integrated into a silicon CMOS based metal oxide sensor device process flow. A hydrogen plasma based surface treatment method is disclosed which allows for selective manipulation of metal oxide based sensors. Our previous disclosures are directed towards an integration method for forming nanobridge based ZnO sensors that involves selectively growing ZnO nanowires from one electrode to another. Although this structure is used in the preferred embodiment to demonstrate reduction of the technique to practice, the technique also certainly applies to nanowire gas sensors fabricated via the "pick and place" method, in which nanowires harvested from a growth substrate are dispersed onto a device substrate with either pre- or post-patterned electrodes, or vertical nanowire based structures, as described in Method to fabricate a nanowire CHEMFET sensor device using selective nanowire deposition of Conley, Jr., et al., Ser. No. 11/115,814, filed Apr. 26, 2005; and Nanowire sensor device structures of Conley, Jr., et al., Ser. No. 11/152,289, filed Jun. 13, 2005, which are also incorporated herein by reference.

Figure 1A:
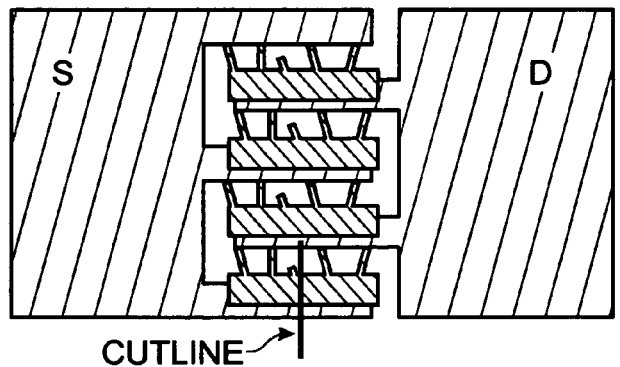
FIGS. 1 and 2 depict prior art metal oxide sensors.
Figure 1B:
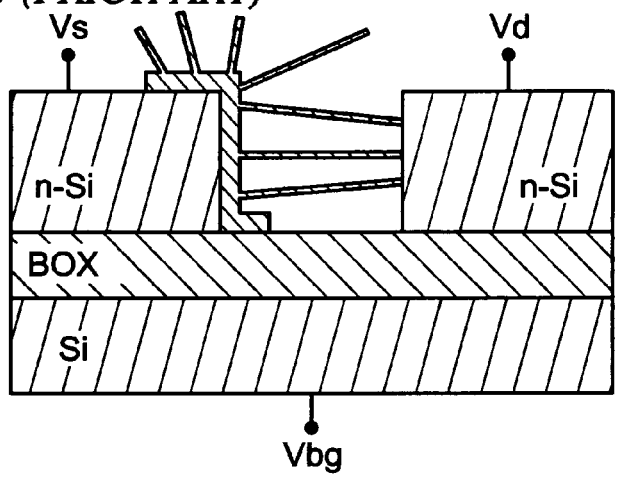

FIG. 1*a* is a top plan view of a prior art horizontal ZnO nanobridge sensor structure. FIG. 1*b* is a side elevation section of a prior art vertical nanobridge structure. These structures were fabricated using a direct integration method involving selective growth of ZnO nanowires, as described in the prior, co-pending patent applications.

Figure 2:
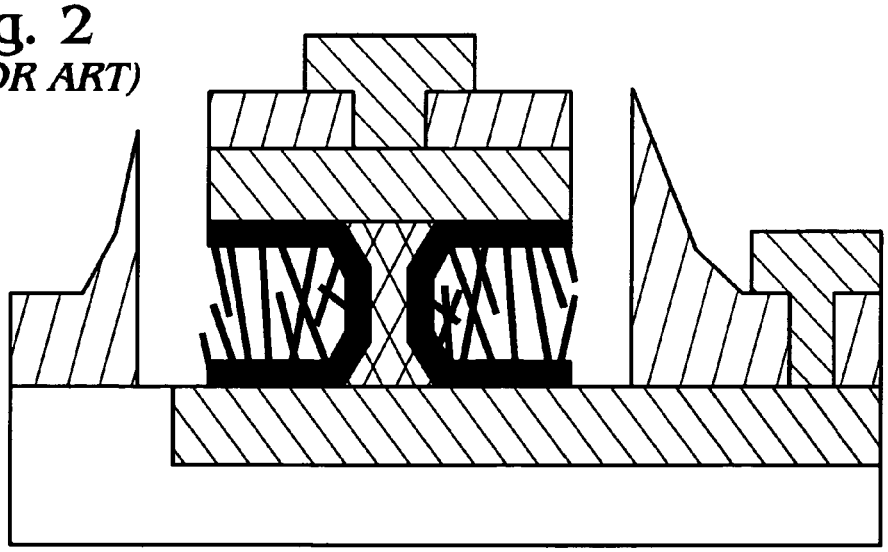

When operated as three terminal devices, as shown in FIG. 2, an as-grown horizontal sensor structure exhibits sensitivity to air and clean dry air (CDA) ambients and $N_2$ purges as shown in the plot of current vs. time vs. temperature, FIGS. 3-7. It is seen that conductivity is reduced after exposure to air and CDA. Conductivity is recovered by $N_2$ purging. The gas sensing properties of ZnO are well known, as described in the above-cited references.

Figure 3:
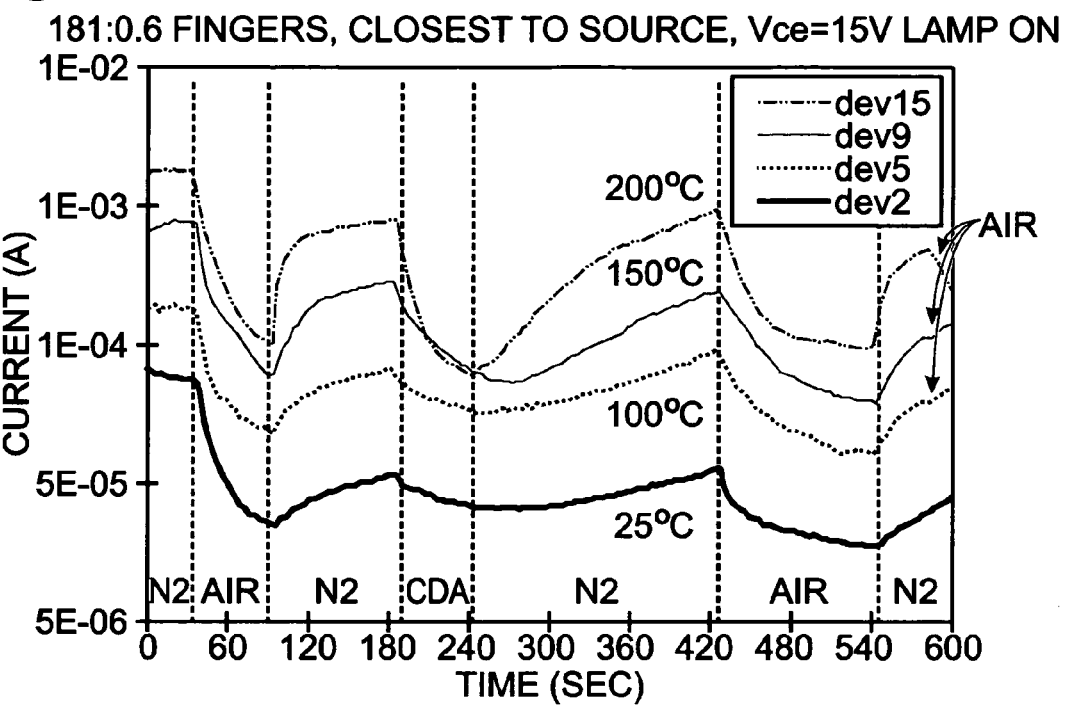
FIGS. 3-7 are graphs depicting properties of metal oxide sensors before and after treatment according to the method of the invention.
Figure 4:
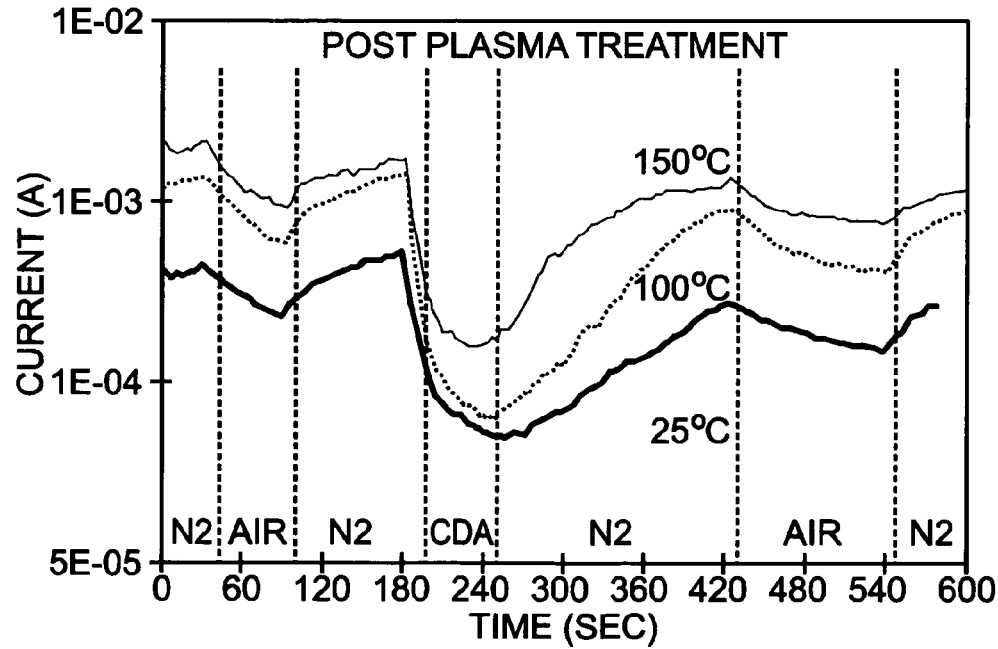
Figure 5:
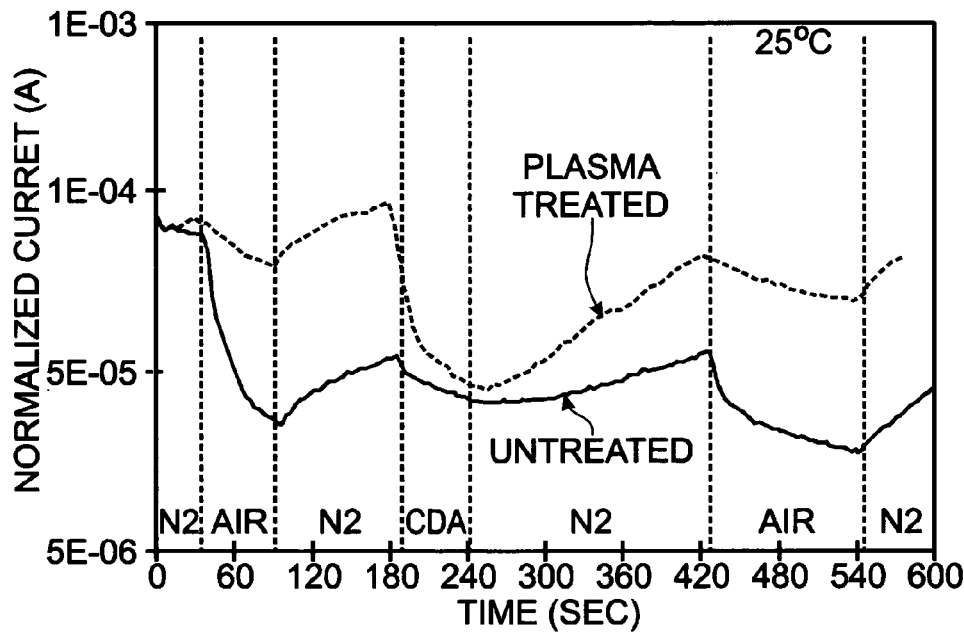

The current vs. time vs. temp for exposure to various ambients is shown in FIGS. 3-5 for as-grown nanowire and for nanobridge structures exposed to a $H_2$ plasma for 2 minutes. It should be noted that other forms of plasma may be used in the method of the invention, and that the specific plasma parameters are for the results depicted in the figures. The $H_2$ plasma includes an inductively coupled plasma discharge operated at 100 mTorr with a 50 sccm pure hydrogen flow. A 13.56 MHz RF at a power of 700 W is applied over an eight square inch area over a six inch wafer chuck. It has recently been reported that $H_2$ plasma ($O_2$ plasma) treatment of ZnO thin films can result in improved (decreased) conductivity, Woldena et al., *Infrared detection of hydrogen-generated free carriers in polycrystalline ZnO thin films*, Appl. Phys. Lett. 97, 043522 (2005), wherein the authors describes a hydrogen and oxygen plasma treatment to improve/decrease n-conductivity of ZnO, however, the authors do not discuss application to nanostructures or any potential effects on gas sensing.

Figure 6:
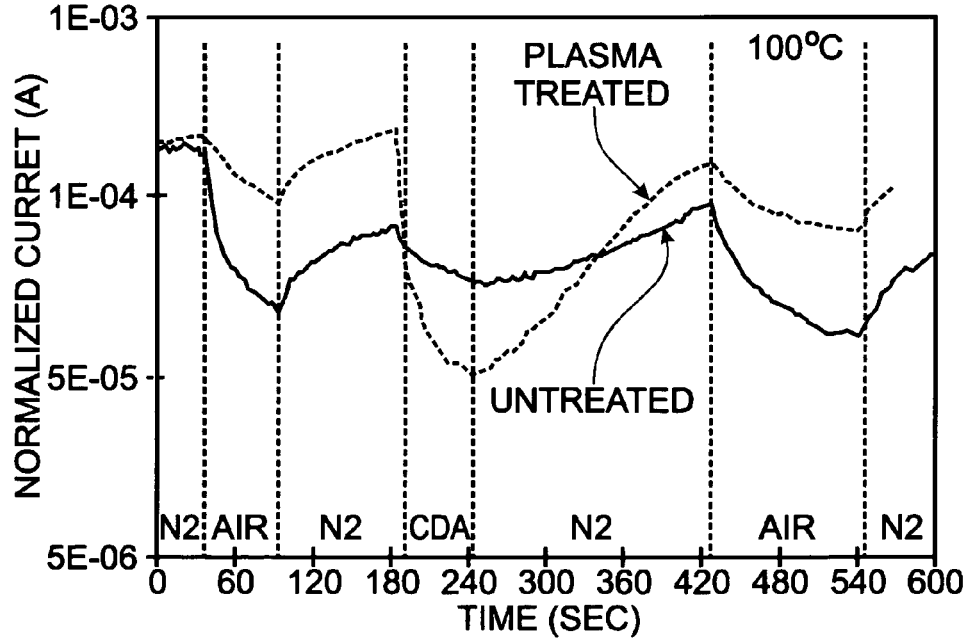
Figure 7:
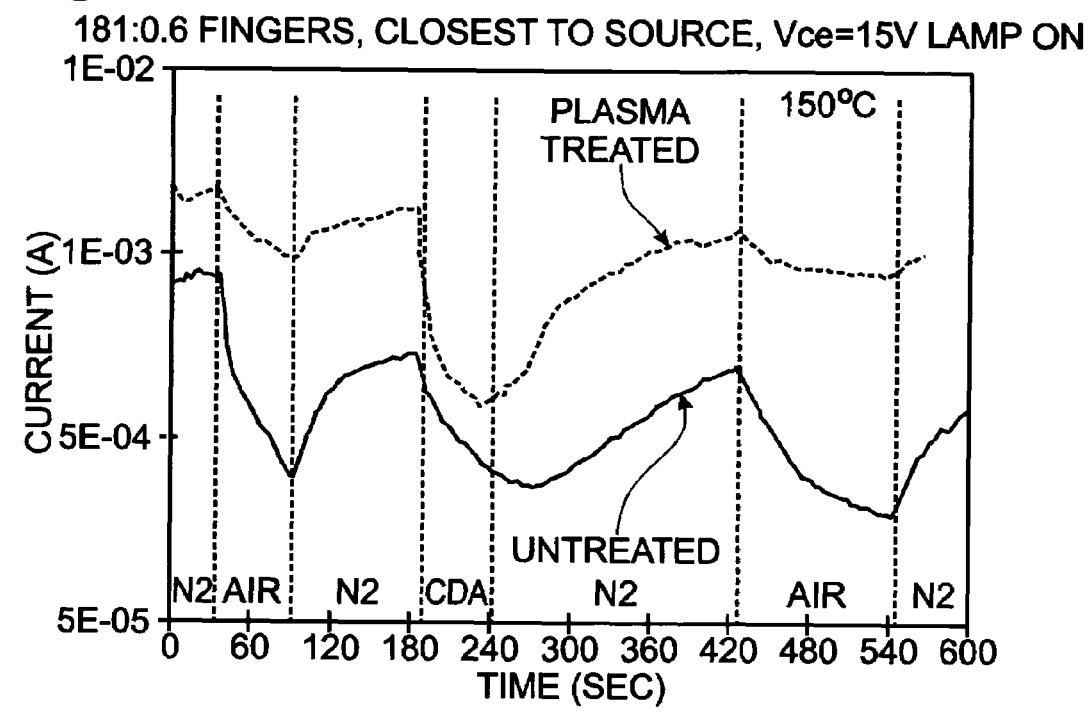

After the $H_2$ plasma exposure, it is observed that several changes have taken place. Comparing FIG. 3 with FIG. 4, it is seen that the $H_2$ plasma exposure resulted in approximately a one order of magnitude increase in conductivity. This increase in conductivity is expected based on Woldena et al. In FIGS. 5-7, the pre and post plasma response at 25° C., 100° C., and 150° C. is compared by replotting on a normalized current scale. It is seen that in addition to the expected increase in conductivity, the gas sensitivity of the device has been altered. In all cases, it is seen that plasma treatment makes the device less sensitive to air, i.e., a smaller decrease in conductivity is observed after air exposure. Recovery appears to take place at the same rate. On the other hand, $H_2$ plasma exposure makes the device more sensitive to CDA, i.e., a greater decrease in conductivity is observed. The behavior at 25° C., 100° C., and 150° C. is qualitatively the same. The treatment appears to be robust as elevated temperature operation does not appear to destroy or inhibit the effects.

Although the crude measurements discussed show a sensitivity change only for two poorly defined ambients, in principle this treatment may be used selectively to tune the sensor for many gases.

Plasma treatment may be followed by metallization and complete integration into a gas sensor device structure. Plasma treatment may also be applied after device formation is complete. Plasma treatment may be selectively applied to ZnO nanowire devices via lithographic patterning prior to treatment to allow for different sensitivities of devices in an array. Barrier materials may also be placed around selected nanowire devices to act as semi-permeable or non-permeable membranes for selective gases to increase the variety of gases that can be sensed. It is likely that other plasma treatments such as $O_2$ will also impact selectivity. These other treatments may be combined to form a selective array of ZnO sensors, each selective to a particular component.

Although a particular structure is used in the preferred embodiment to demonstrate reduction of the technique to practice, this method also certainly applies to nanowire gas sensors fabricated via the "pick and place" method in which nanowires harvested from a growth substrate are dispersed onto a device substrate with either pre- or post-patterned electrodes, vertical nanowire based structures, or other imaginable nano or thin film based structures.

Thus, a method for enhancing sensitivity of metal oxide sensors has been disclosed. It will be appreciated that further variations and modifications thereof may be made within the scope of the invention as defined in the appended claims.

We claim:

1. A method of selectively enhancing the sensitivity of a metal oxide sensor, comprising:
   fabricating a metal oxide sensor and a sensor element therein;
   exposing the sensor element to a $H_2$ plasma stream using an inductively coupled plasma discharge; and,
   wherein the $H_2$ plasma stream is operated at about 100 mTorr, with a 50 sccm pure hydrogen flow, and at a 13.56 MHz RF at a power of 700 W.

2. The method of claim 1 wherein said fabricating a metal oxide sensor and a sensor element therein includes fabricating a ZnO sensor.

3. The method of claim 2 wherein said fabricating a metal oxide sensor and a sensor element therein includes fabricating a ZnO nanostructure sensor.

4. The method of claim 3 wherein said exposing the sensor element to a plasma stream includes lithographic patterning of the sensor element prior to said exposing.

5. A method of selectively enhancing the sensitivity of a metal oxide sensor, comprising:
   fabricating a ZnO sensor having a ZnO sensor element therein; and
   exposing the ZnO sensor element to a $H_2$ plasma stream using an inductively coupled plasma discharge; and,
   wherein the $H_2$ plasma stream is operated at about 100 mTorr, with a 50 sccm pure hydrogen flow, and at a 13.56 MHz RF at a power of 700 W.

6. The method of claim 5 wherein said fabricating a ZnO sensor and a ZnO sensor clement therein includes fabricating a ZnO nanostructure sensor.

7. The method of claim 5 wherein said exposing the ZnO sensor element to a plasma stream includes lithographic patterning of the ZnO sensor element prior to said exposing.

* * * * *